(12) United States Patent
Tomaru

(10) Patent No.: US 7,623,231 B2
(45) Date of Patent: Nov. 24, 2009

(54) DEVICE FOR RAMAN SPECTROSCOPY AND RAMAN SPECTROSCOPIC APPARATUS

(75) Inventor: Yuichi Tomaru, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 254 days.

(21) Appl. No.: 11/353,107

(22) Filed: Feb. 14, 2006

(65) Prior Publication Data
US 2006/0181701 A1    Aug. 17, 2006

(30) Foreign Application Priority Data
Feb. 14, 2005    (JP)    ............... 2005-035564

(51) Int. Cl.
*G01J 3/44*    (2006.01)
(52) U.S. Cl. .................................. 356/301
(58) Field of Classification Search ............... 356/301; 427/250, 255.7, 258, 271, 287, 405, 419.2
See application file for complete search history.

(56) References Cited

U.S. PATENT DOCUMENTS 5,376,556 A    12/1994    Tarcha et al.
6,739,930 B2 *    5/2004    Cheng et al. .................. 445/24
2005/0105085 A1 *    5/2005    Naya .......................... 356/301

FOREIGN PATENT DOCUMENTS

JP    2004-170334 A    6/2004

* cited by examiner

*Primary Examiner*—Gregory J Toatley, Jr.
*Assistant Examiner*—Abdullahi Nur
(74) *Attorney, Agent, or Firm*—Sughrue Mion, PLLC

(57) ABSTRACT

A device for Raman spectroscopy comprises a fine structure body provided with an array structure region, in which a plurality of recess areas having approximately identical shapes, as viewed from above, are arrayed regularly at approximately identical pitches. A surface of the fine structure body on the side of the array structure region acts as a light scattering surface. The fine structure body may be constituted of an un-anodized part of a metal body to be subjected to anodic oxidation processing, the un-anodized part remaining after a processing, wherein the anodic oxidation processing is performed on the metal body, a part of the metal body being thereby converted into a metal oxide layer, and wherein the metal oxide layer is removed from the metal body, has been performed.

8 Claims, 4 Drawing Sheets

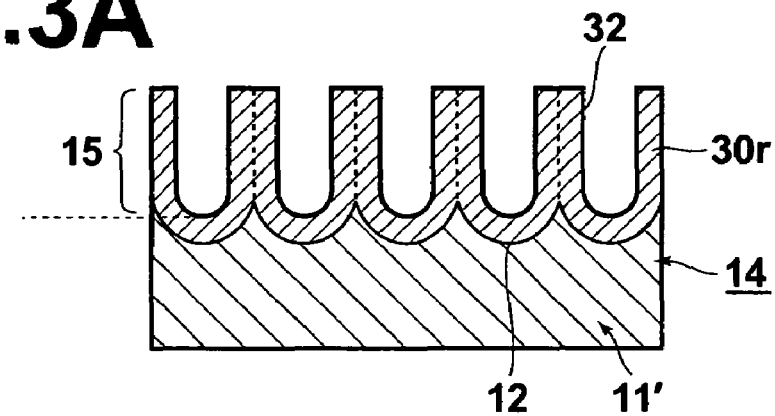
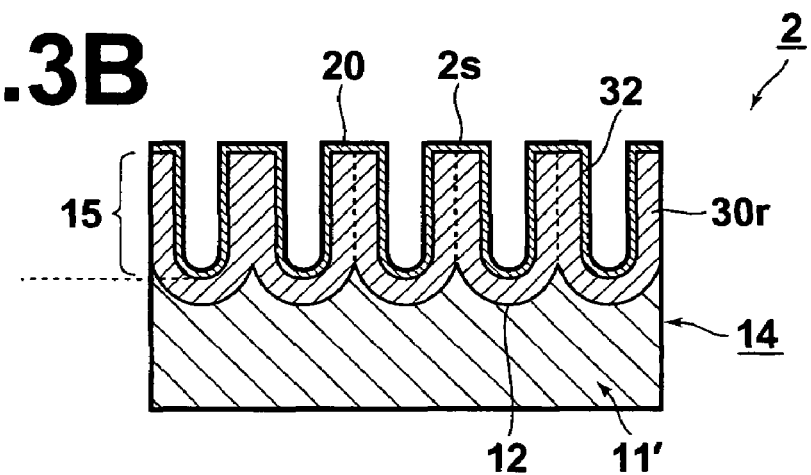
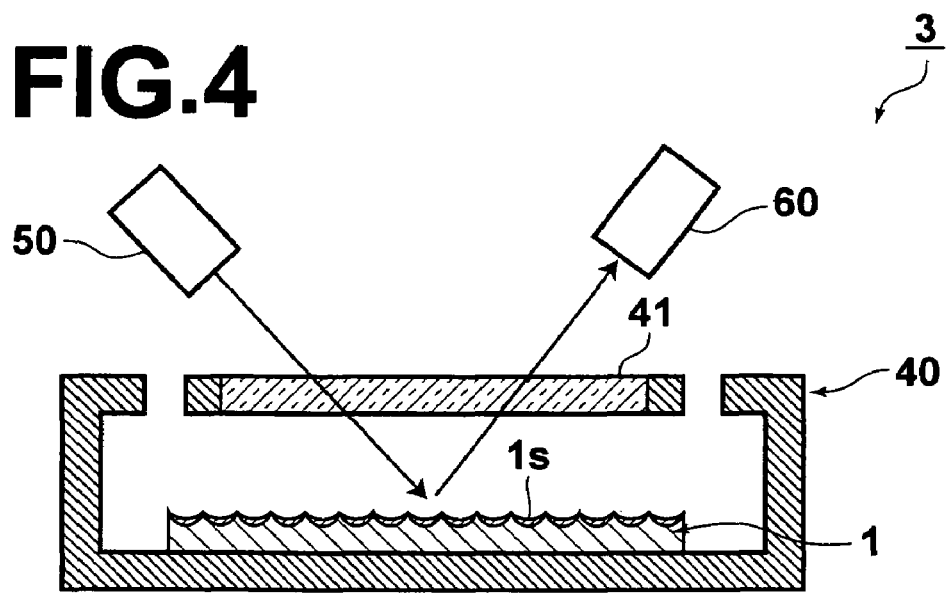

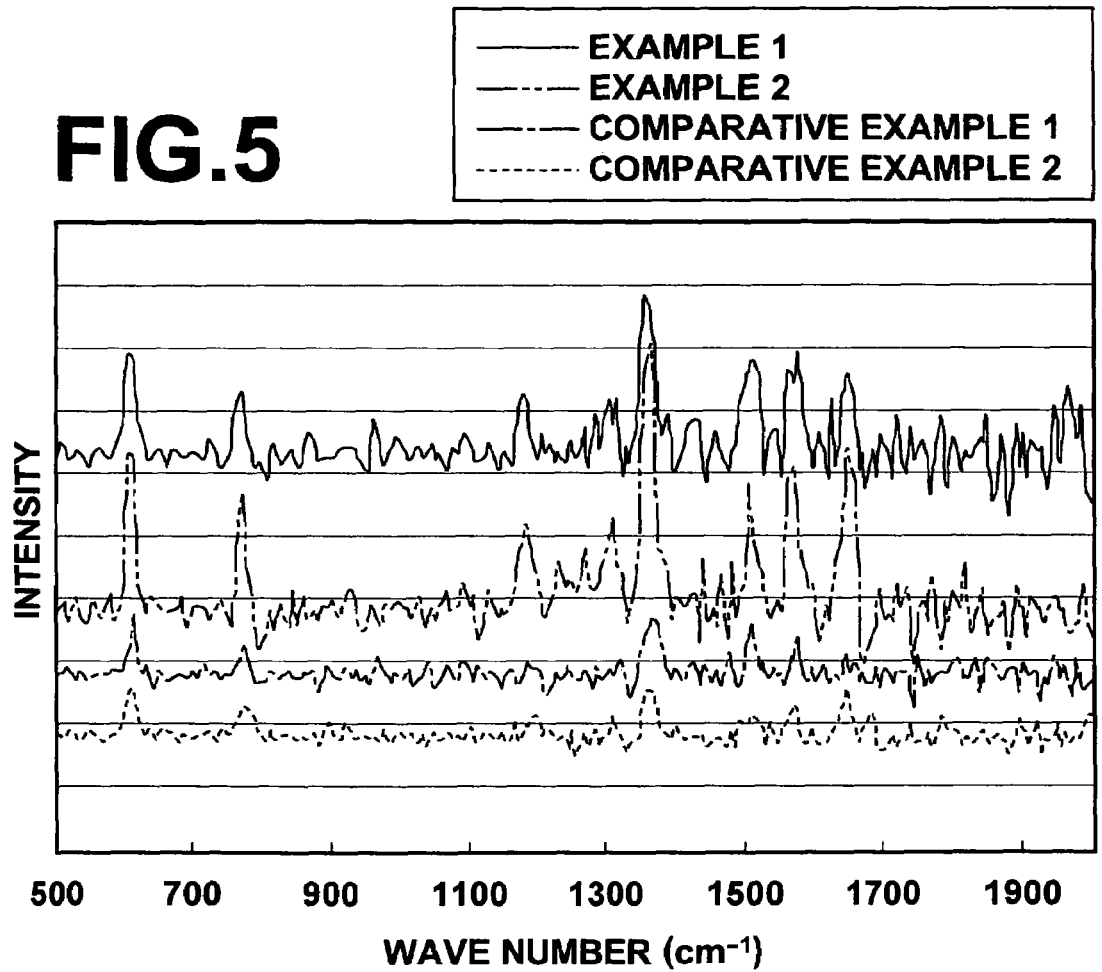

DEVICE FOR RAMAN SPECTROSCOPY AND RAMAN SPECTROSCOPIC APPARATUS

BACKGROUND OF THE INVENTION

1. Field of the Invention

This invention relates to a device for Raman spectroscopy, which has a surface recess-protrusion structure. This invention also relates to a Raman spectroscopic apparatus, in which the device for Raman spectroscopy is utilized.

2. Description of the Related Art

Raman spectroscopy is a technique, wherein scattered light, which is obtained from irradiation of single-wavelength light to a substance, is separated into spectral components of the scattered light, and wherein a spectrum (i.e., a Raman spectrum) of Raman scattered light is thereby obtained. The Raman spectroscopy is utilized for identification of a substance, and the like. The Raman scattered light is weak light. However, it has been known that, in cases where light is irradiated to a substance in a state in which the substance is in contact with a metal body, particularly a metal body having a surface provided with fine recesses and protrusions, the intensity of the Raman scattered light is boosted.

As devices for Raman spectroscopy, which have a light scattering surface for scattering incident light, there have heretofore been known (1) a device for Raman spectroscopy comprising a metal body, whose surface has been electrochemically roughed at random by the utilization of oxidation-reduction reactions, or the like, and (2) a device for Raman spectroscopy, comprising a metal body having a surface, to which fine metal particles have been fixed at random. (The aforesaid devices for Raman spectroscopy described under (1) and (2) are described in, for example, U.S. Pat. No. 5,376,556.)

Also, there has heretofore been known (3) a device for Raman spectroscopy comprising a metal body having a surface, to which metal-coated fine particles have been fixed regularly. The aforesaid device for Raman spectroscopy described under (3) may be produced with a process comprising the steps of: forming a particle layer, which is provided with periodically arrayed fine particles of silica, or the like, on a base plate, introducing the base plate provided with the particle layer into a solution containing a metal and a polymer, taking the base plate provided with the particle layer out of the solution, drying the base plate provided with the particle layer, and firing the particle layer at a temperature, at which the polymer is capable of being burned out and at which the metal is capable of being fixed to the fine particles without agglomerating, the metal-coated fine particles being thereby fixed to the base plate. (The aforesaid device for Raman spectroscopy described under (3) and the aforesaid process for producing the device for Raman spectroscopy are described in, for example, Japanese Unexamined Patent Publication No. 2004-170334.)

However, with the aforesaid conventional techniques described under (1) and (2), which are described in, for example, U.S. Pat. No. 5,376,556, the problems are encountered in that, since the surface recesses and protrusions are formed at random, intra-plane non-uniformity occurs with the Raman scattering intensity. Therefore, detection of the Raman scattered light is not capable of being kept reliable, and high-accuracy measurements are not always capable of being performed reliably.

With the aforesaid conventional techniques described under (3), which are described in, for example, Japanese Unexamined Patent Publication No. 2004-170334, the metal-coated fine particles are regularly fixed to the surface of the base plate, and therefore the problems described above are capable of being eliminated. However, it is not always possible to perform each of the steps of: (a) forming the particle layer, which is provided with periodically arrayed fine particles having a size of a nano-order, or the like, on the base plate, (b) introducing the base plate provided with the particle layer into the solution containing the metal and the polymer, and taking the base plate provided with the particle layer out of the solution, such that the array of the fine particles, which have not been fixed to the base plate, may be kept, and (c) controlling the firing of the particle layer, burning out the polymer, and fixing the metal to the fine particles, such that the metal may not agglomerate. Therefore, with the aforesaid conventional techniques described under (3), which are described in, for example, Japanese Unexamined Patent Publication No. 2004-170334, the process for producing the device for Raman spectroscopy is not capable of being kept simple.

SUMMARY OF THE INVENTION

The primary object of the present invention is to provide a device for Raman spectroscopy, which exhibits high intra-plane uniformity of Raman scattering intensity, which enables high-accuracy Raman spectrometry to be performed reliably, and which is easy to produce.

Another object of the present invention is to provide a Raman spectroscopic apparatus, which utilizes the device for Raman spectroscopy.

The present invention provides a first device for Raman spectroscopy, which is adapted for use in Raman spectroscopy for separating scattered light into its spectral components and detecting Raman scattered light, and which is provided with a light scattering surface for scattering incident light, the device for Raman spectroscopy comprising a fine structure body provided with an array structure region, in which a plurality of recess areas having approximately identical shapes, as viewed from above, are arrayed regularly at approximately identical pitches, a surface of the fine structure body on the side of the array structure region acting as the light scattering surface.

The term "approximately identical pitches" as used herein means that the pitches of the recess areas fall within the range of average pitch $P_{ave} \pm 10\%$.

The first device for Raman spectroscopy in accordance with the present invention should preferably be modified such that a Raman scattering boosting substance, which exhibits a Raman scattering intensity higher than the Raman scattering intensity of a constituent material of the array structure region, is fixed to the array structure region side of the fine structure body.

The present invention also provides a second device for Raman spectroscopy, which is adapted for use in Raman spectroscopy for separating scattered light into its spectral components and detecting Raman scattered light, and which is provided with a light scattering surface for scattering incident light, the device for Raman spectroscopy comprising a fine structure body, which is constituted of an un-anodized part of a metal body to be subjected to anodic oxidation processing, the un-anodized part remaining after a processing, wherein the anodic oxidation processing is performed on the metal body to be subjected to the anodic oxidation processing, apart of the metal body to be subjected to the anodic oxidation processing being thereby converted into a metal oxide layer, and wherein the metal oxide layer is removed from the metal body to be subjected to the anodic oxidation processing, has been performed.

The second device for Raman spectroscopy in accordance with the present invention may be modified such that the metal body to be subjected to the anodic oxidation processing is a metal body containing aluminum as a principal constituent, and the fine structure body is provided with an array structure region, in which a plurality of recess areas having approximately regular hexagon shapes, as viewed from above, are arrayed so as to stand close to one another.

The term "principal constituent" as used herein means the constituent of the metal body to be subjected to the anodic oxidation processing, which constituent is contained in a proportion of at least 90% with respect to the metal body to be subjected to the anodic oxidation processing.

The present invention further provides a third device for Raman spectroscopy, which is adapted for use in Raman spectroscopy for separating scattered light into its spectral components and detecting Raman scattered light, and which is provided with a light scattering surface for scattering incident light, the device for Raman spectroscopy comprising a fine structure body, which is constituted of an un-anodized part of a metal body to be subjected to anodic oxidation processing and a remainder of a metal oxide layer, the un-anodized part and the remainder of the metal oxide layer remaining after a processing, wherein the anodic oxidation processing is performed on the metal body to be subjected to the anodic oxidation processing, a part of the metal body to be subjected to the anodic oxidation processing being thereby converted into the metal oxide layer, and wherein a part of the metal oxide layer is removed from the metal body to be subjected to the anodic oxidation processing, has been performed.

The present invention still further provides a Raman spectroscopic apparatus, comprising:

i) a device for Raman spectroscopy in accordance with the present invention, ii) light irradiating means for irradiating light, which has a specific wavelength, to the light scattering surface of the device for Raman spectroscopy, and iii) spectroscopic means for separating the scattered light, which occurs at the light scattering surface, into spectral components of the scattered light, and obtaining a spectrum of Raman scattered light.

The first device for Raman spectroscopy in accordance with the present invention comprises the fine structure body provided with the array structure region, in which the plurality of the recess areas having approximately identical shapes, as viewed from above, are arrayed regularly at approximately identical pitches. Also, the surface of the fine structure body on the side of the array structure region acts as the light scattering surface. Therefore, with the first device for Raman spectroscopy in accordance with the present invention, the uniformity of the surface recesses and protrusions is capable of being kept high, the intra-plane uniformity of the Raman scattering intensity is capable of being kept high, and high-accuracy Raman spectrometry is capable of being performed reliably.

Also, with the first device for Raman spectroscopy in accordance with the present invention, the recess areas are formed regularly, and the regular surface recess-protrusion structure is formed. Therefore, the first device for Raman spectroscopy in accordance with the present invention has the advantages over the conventional technique described in, for example, Japanese Unexamined Patent Publication No. 2004-170334, wherein the metal-coated fine particles are fixed to the surface of the base plate, and wherein the regular surface recess-protrusion structure is thereby formed, in that the device for Raman spectroscopy is capable of being produced easily.

With each of the second and third devices for Raman spectroscopy in accordance with the present invention, by the utilization of the characteristics of the anodic oxidation processing in that the metal oxide layer having regular array characteristics is capable of being formed, at least a part of the metal oxide layer is removed, and the remaining part is utilized as the fine structure body. Therefore, the device for Raman spectroscopy provided with the fine structure body having the regular surface recess-protrusion structure is capable of being produced easily.

BRIEF DESCRIPTION OF THE DRAWINGS

FIG. 3A is a sectional view corresponding to FIG. 2C and showing the un-anodized part of the metal body to be subjected to the anodic oxidation processing and a remainder of the metal oxide layer, which remainder remains after a part of the metal oxide layer has been removed from the metal body to be subjected to the anodic oxidation processing, FIG. 3B is a sectional view corresponding to FIG. 2D and showing the un-anodized part of the metal body to be subjected to the anodic oxidation processing and the remainder of the metal oxide layer, the remainder having a surface, to which a Raman scattering boosting substance has been fixed, FIG. 4 is a sectional view showing an embodiment of a Raman spectroscopic apparatus in accordance with the present invention, and FIG. 5 is a diagram showing Raman spectra obtained with devices for Raman spectroscopy produced in Examples 1 and 2 and Comparative Examples 1 and 2.

DESCRIPTION OF THE PREFERRED EMBODIMENTS

The present invention will hereinbelow be described in further detail with reference to the accompanying drawings.

First Embodiment of the Device for Raman Spectroscopy

Figure 1A:
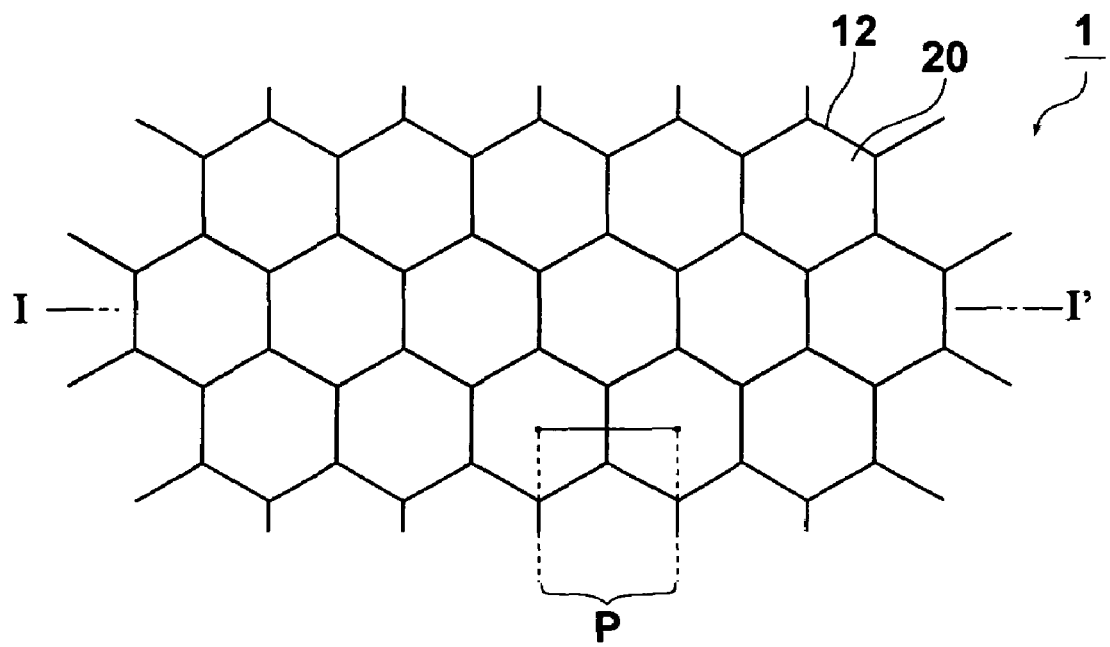
FIG. 1A is a plan view showing a first embodiment of the device for Raman spectroscopy in accordance with the present invention.
Figure 1B:
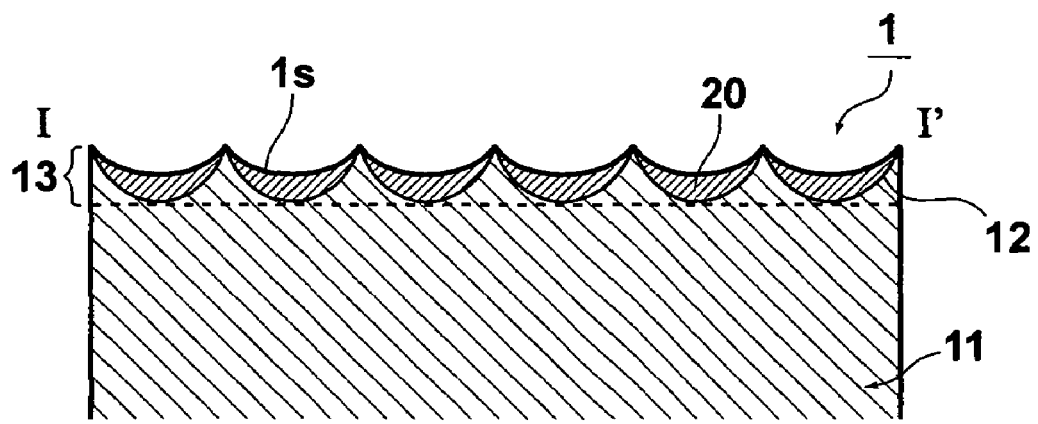
FIG. 1B is a sectional view taken on line I-I' of FIG. 1A.
Figure 2A:
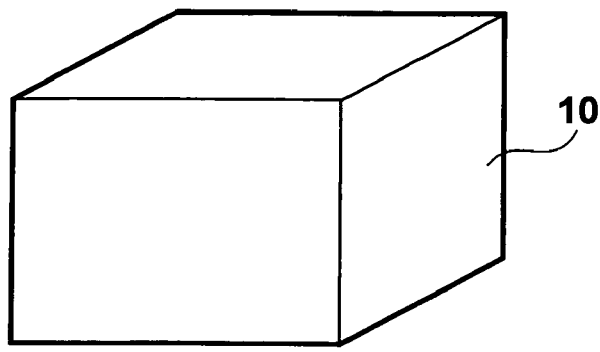
FIG. 2A is a perspective view showing a metal body to be subjected to the anodic oxidation processing, which metal body is utilized for production of the first embodiment of the device for Raman spectroscopy in accordance with the present invention.
Figure 2B:
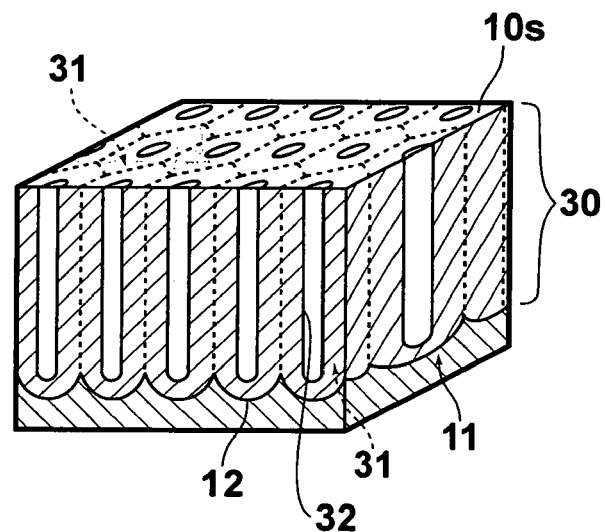
FIG. 2B is a perspective view showing the metal body to be subjected to the anodic oxidation processing, which metal body has been subjected to the anodic oxidation processing and a part of which has been converted into a metal oxide layer.
Figure 2C:
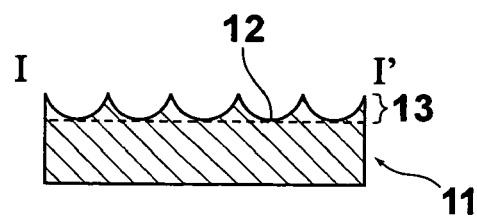
FIG. 2C is a sectional view corresponding to FIG. 1B and showing an un-anodized part of the metal body to be subjected to the anodic oxidation processing, which un-anodized part remains after the metal oxide layer has been removed from the metal body to be subjected to the anodic oxidation processing.
Figure 2D:
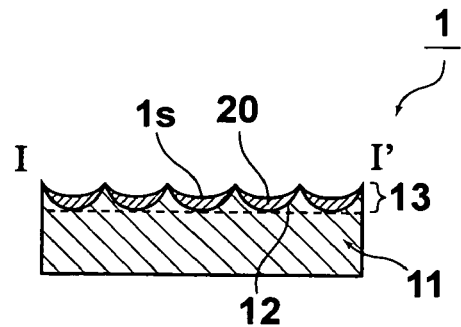
FIG. 2D is a sectional view corresponding to FIG. 1B and showing the un-anodized part of the metal body to be subjected to the anodic oxidation processing, the un-anodized part having a surface, to which a Raman scattering boosting substance has been fixed.

FIG. 1A is a plan view showing a first embodiment of the device for Raman spectroscopy in accordance with the present invention. FIG. 1B is a sectional view taken on line I-I' of FIG. 1A. FIG. 2A is a perspective view showing a metal body to be subjected to the anodic oxidation processing, which metal body is utilized for production of the first embodiment of the device for Raman spectroscopy in accordance with the present invention. FIG. 2B is a perspective view showing the metal body to be subjected to the anodic oxidation processing, which metal body has been subjected to the anodic oxidation processing and a part of which has been converted into a metal oxide layer. FIG. 2C is a sectional view corresponding to FIG. 1B and showing an un-anodized part of the metal body to be subjected to the anodic oxidation processing, which un-anodized part remains after the metal oxide layer has been removed from the metal body to be subjected to the anodic oxidation processing. FIG. 2D is a sectional view corresponding to FIG. 1B and showing the un-anodized part of the metal body to be subjected to the anodic oxidation processing, the un-anodized part having a surface, to which a Raman scattering boosting substance has been fixed.

A device for Raman spectroscopy 1, which is a first embodiment of the device for Raman spectroscopy in accordance with the present invention, is adapted for use in Raman spectroscopy for separating scattered light into its spectral components and detecting Raman scattered light. The device for Raman spectroscopy 1 is provided with a light scattering surface for scattering incident light.

As illustrated in FIG. 1A and FIG. 1B, the device for Raman spectroscopy 1 comprises a fine structure body 11 provided with an array structure region 13. The array structure region 13 is provided with a plurality of dimple-shaped recess areas 12, 12, . . . having approximately identical shapes, as viewed from above. The dimple-shaped recess areas 12, 12, . . . are arrayed regularly at approximately identical pitches P. Also, a Raman scattering boosting substance 20, which exhibits a Raman scattering intensity higher than the Raman scattering intensity of a constituent material of the array structure region 13, is fixed to the surface of the array structure region 13 and along the surface recess-protrusion shape of the array structure region 13.

The surface of the device for Raman spectroscopy 1 on the side of the array structure region 13 acts as a light scattering surface 1s. Each of the dimple-shaped recess areas 12, 12, . . . constituting the array structure region 13 has an approximately regular hexagon shape, as viewed from above. The dimple-shaped recess areas 12, 12, . . . are arrayed so as to stand close to one another. Specifically, the dimple-shaped recess areas 12, 12, . . . are arrayed such that six dimple-shaped recess areas 12, 12, . . . are adjacent to one dimple-shaped recess area 12.

The device for Raman spectroscopy 1 may be produced with a process illustrated in FIG. 2A, FIG. 2B, FIG. 2C, and FIG. 2D. Specifically, as illustrated in FIG. 2A, a metal body 10 to be subjected to the anodic oxidation processing is utilized for the production of the device for Raman spectroscopy 1. The metal body 10 to be subjected to the anodic oxidation processing contains aluminum (Al) as a principal constituent and may contain a trace amount of impurities. The anodic oxidation processing is performed on the metal body 10 to be subjected to the anodic oxidation processing. With the anodic oxidation processing, as illustrated in FIG. 2B, a part of the metal body 10 to be subjected to the anodic oxidation processing is converted into an alumina ($Al_2O_3$) layer (i.e., a metal oxide layer) 30. Also, as illustrated in FIG. 2C, the alumina layer 30 is removed from the metal body 10 to be subjected to the anodic oxidation processing. An un-anodized part of the metal body 10 to be subjected to the anodic oxidation processing remains after the removal of the alumina layer 30. The un-anodized part of the metal body 10 to be subjected to the anodic oxidation processing is utilized as the fine structure body 11. Ordinarily, the thickness of the alumina layer 30 formed with the anodic oxidation processing is smaller than the thickness of the un-anodized part of the metal body 10 to be subjected to the anodic oxidation processing. However, in FIG. 2B, for clearness, the thickness of the alumina layer 30 is illustrated to be large.

No limitation is imposed upon the shape of the metal body 10 to be subjected to the anodic oxidation processing. By way of example, the metal body 10 to be subjected to the anodic oxidation processing may have a planar shape, or the like. Alternatively, the metal body 10 to be subjected to the anodic oxidation processing may be formed in a layer form on a support and may be utilized in this form.

By way of example, the anodic oxidation processing may be performed in the manner described below. Specifically, the metal body 10 to be subjected to the anodic oxidation processing is set as an anode, and carbon, aluminum, or the like, is set as a cathode (i.e., an opposite electrode). The metal body 10 to be subjected to the anodic oxidation processing, i.e. the anode, and the cathode are immersed in an electrolyte for anodic oxidation processing, and a voltage is applied across the anode and the cathode. No limitation is imposed upon the kind of the electrolyte. However, the electrolyte should preferably be an acidic electrolyte containing at least one kind of acid selected from the group consisting of sulfuric acid, phosphoric acid, chromic acid, oxalic acid, sulfamic acid, benzenesulfonic acid, and amidosulfonic acid.

As illustrated in FIG. 2B, in cases where the anodic oxidation processing is performed on the metal body 10 to be subjected to the anodic oxidation processing, the oxidation reaction advances from a surface 10s (i.e., the top surface in FIG. 2B) toward the direction approximately normal to the surface 10s. The alumina layer 30 is formed in this manner.

The alumina layer 30 having been formed with the anodic oxidation processing has a structure, in which fine pillar-shaped bodies 31, 31, . . . having approximately regular hexagon shapes, as viewed from above, are arrayed so as to stand close to one another. At an approximately middle area of each of the fine pillar-shaped bodies 31, 31, . . . , a fine hole 32 extending in the depth direction from the surface 10s is formed. Also, as illustrated in FIG. 2B, a bottom surface of each of the fine pillar-shaped bodies 31, 31, . . . has a round shape. The dimple-shaped recess areas 12, 12, . . . described above are thus formed on the surface of the un-anodized part of the metal body 10 to be subjected to the anodic oxidation processing, which surface stands facing the alumina layer 30. The structure of the alumina layer, which is formed with the anodic oxidation processing, is described in, for example, "Preparation of Meso-porous Alumina with Anodic Oxidation Technique and Application as Functional Materials" by Hideki Masuda, Material Technology, Vol. 15, No. 10, p. 34, 1997.

The pitches of the fine pillar-shaped bodies 31, 31, . . . constituting the alumina layer 30 directly determine the pitches P of the dimple-shaped recess areas 12, 12, . . . of the fine structure body 11. Also, the thickness of the round bottom area of each of the fine pillar-shaped bodies 31, 31, . . . determines the depth of each of the dimple-shaped recess areas 12, 12, . . . For example, the pitches P of the dimple-shaped recess areas 12, 12, . . . fall within the range of approximately 10 nm to approximately 500 nm, and the depth of each of the dimple-shaped recess areas 12, 12, . . . falls within the range of 5 nm to 250 nm.

Ordinary anodic oxidation processing aims at forming the alumina layer 30 (i.e., the meso-porous alumina layer) having the fine holes 32, 32, . . . Therefore, with the ordinary anodic oxidation processing, it is necessary that the oxidation reaction is allowed to advance to some extent, and the alumina layer 30 having a thickness appropriate for the purpose of use is formed. However, in this embodiment, the anodic oxidation processing is performed for forming the dimple-shaped recess areas 12, 12, . . . on the un-anodized part of the metal body 10 to be subjected to the anodic oxidation processing, and the alumina layer 30 having been formed with the anodic oxidation processing is removed. Therefore, in this embodiment, it is sufficient for the alumina layer 30 to the minimum thickness, such that the dimple-shaped recess areas 12, 12, . . . are capable of being formed reliably.

Therefore, the conditions for the anodic oxidation processing may be designed appropriately, such that the un-anodized part may remain, and such that the dimple-shaped recess areas 12, 12, . . . maybe formed reliably on the surface of the un-anodized part. In cases where oxalic acid is utilized as the electrolyte, the conditions for the anodic oxidation processing may be set such that the electrolyte concentration is 0.5M, the electrolyte temperature is 15° C., and the applied voltage is 40V. With alteration of the time of the electrolysis, the alumina layer 30 having an arbitrary layer thickness is capable of being formed. In cases where the thickness of the metal body 10 to be subjected to the anodic oxidation processing before the anodic oxidation processing is performed is set to be larger than the thickness of the formed alumina layer 30, the un-anodized part remains, and the fine structure body 11 is capable of being obtained.

One of various techniques may be employed for selectively removing the alumina layer 30, such that the un-anodized part of the metal body 10 to be subjected to the anodic oxidation processing may remain. For example, it is possible to employ a wet etching technique, wherein an etching liquid (such as a chromic acid solution) capable of selectively dissolving alumina is utilized. Alternatively, a technique maybe employed, wherein a voltage is applied reversely across the metal body 10 to be subjected to the anodic oxidation processing and the opposite electrode after the anodic oxidation processing has been performed.

As the Raman scattering boosting substance 20, a substance having the Raman scattering boosting effects with a localized plasmon resonance phenomenon is capable of being utilized preferably. In the localized plasmon resonance phenomenon, free electrons at a protruding area undergo resonance with an electric field of light and vibrate, and a strong electric field thus occurs in the vicinity of the protruding area. It is considered that the Raman scattering is boosted by the occurring electric field of the light. The localized plasmon resonance phenomenon occurs with various kinds of metals, which have the free electrons. Among the various kinds of metals, which have the free electrons, metals having comparatively large Raman scattering boosting effects are preferable. Also, the Raman scattering boosting substance 20 should preferably be constituted of a metal, which has the Raman scattering boosting effects, a high chemical stability (i.e., the high stability with respect to a sample), and little adverse effect upon a Raman scattering signal. Specifically, the Raman scattering boosting substance 20 should preferably be constituted of gold (Au), silver (Ag), copper (Cu), platinum (Pt), nickel (Ni), titanium (Ti), or the like. Among the above-enumerated metals, gold (Au) and silver (Ag) are particularly preferable for their large Raman scattering boosting effects.

As the technique for fixing the Raman scattering boosting substance 20 to the surface of the array structure region 13, one of various fixing techniques may be employed. For example, a coating technique may be employed, wherein a liquid, which contains the Raman scattering boosting substance 20 and, when necessary, a binder, such as a resin, is applied onto the surface of the array structure region 13 and dried. Alternatively, a vacuum evaporation technique may be employed, wherein the Raman scattering boosting substance 20 is vacuum deposited onto the surface of the array structure region 13.

No limitation is imposed upon the form in which the Raman scattering boosting substance 20 is fixed to the surface of the array structure region 13. For example, a plurality of particles of the Raman scattering boosting substance 20 may be fixed to the surface of the array structure region 13. Alternatively, the Raman scattering boosting substance 20 may be fixed in a layer form together with a binder to the surface of the array structure region 13.

As described above, this embodiment of the device for Raman spectroscopy 1 comprises the fine structure body 11 provided with the array structure region 13. The array structure region 13 is provided with the plurality of the dimple-shaped recess areas 12, 12, . . . having approximately regular hexagon shapes, as viewed from above. The dimple-shaped recess areas 12, 12, . . . are arrayed regularly at the approximately identical pitches P. Also, the Raman scattering boosting substance 20 is fixed to the surface of the array structure region 13 and along the surface recess-protrusion shape of the array structure region 13. Therefore, the light scattering surface 1s has the surface recess-protrusion shape pattern identical with the recess-protrusion shape pattern of the array structure region 13.

The device for Raman spectroscopy 1 thus has the light scattering surface 1s having the nano-order recess-protrusion pattern. Therefore, the device for Raman spectroscopy 1 has the Raman scattering boosting effects larger than the Raman scattering boosting effects of a device for Raman spectroscopy having a flat light scattering surface (e.g., the Raman scattering boosting effects at least ten times as large as the Raman scattering boosting effects of the device for Raman spectroscopy having the flat light scattering surface). The large Raman scattering boosting effects are presumably due to the increase in the surface area by virtue of the surface recess-protrusion pattern and due to the localized plasmon resonance phenomenon. As described above, the localized plasmon resonance phenomenon is the phenomenon in which the free electrons at the protruding area undergo the resonance with the electric field of the light and vibrate, and in which the strong electric field thus occurs in the vicinity of the protruding area.

Since the Raman scattering boosting substance 20 has been fixed to the array structure region 13, the localized plasmon resonance phenomenon is capable of occurring efficiently, and the high level of the Raman scattering boosting effects are capable of being obtained. However, the fine structure body 11 contains Al as the principal constituent, and the localized plasmon resonance phenomenon also occurs with Al. Therefore, by virtue of the surface recess-protrusion structure of the fine structure body 11 and the Raman scattering boosting effects of Al, in cases where the Raman scattering boosting substance 20 is not fixed to the array structure region 13, good Raman scattering boosting effects are capable of being obtained. Also, in lieu of the Raman scattering boosting substance 20, which has the Raman scattering intensity higher than the Raman scattering intensity of the fine structure body 11, being fixed to the array structure region 13, Al utilized as the principal constituent of the fine structure body 11 may be fixed to the array structure region 13.

With this embodiment of the device for Raman spectroscopy 1, the light scattering surface 1s has high intra-plane uniformity of the recess-protrusion pattern. Therefore, the intra-plane uniformity of the Raman scattering intensity is capable of being kept high, and the Raman spectrometry is capable of being performed reliably. Further, with this embodiment of the device for Raman spectroscopy 1, wherein the light scattering surface 1s has high intra-plane uniformity of the recess-protrusion pattern, it is possible to obtain the Raman scattering boosting effects larger than the Raman scattering boosting effects obtained with the conventional technique in which the surface recesses and protrusions are formed at random.

The occurrence of the localized plasmon resonance phenomenon depends upon the size of each of the recess areas having been formed on the surface of the fine structure body. In this embodiment, the uniformity of the sizes of the plurality of the dimple-shaped recess areas 12, 12, . . . having been formed on the surface of the fine structure body 11 is high. Accordingly, it is presumed that the localized plasmon resonance phenomenon occurs efficiently within all of the dimple-shaped recess areas 12, 12, . . . , and therefore the Raman scattering boosting effects are capable of being obtained, which are larger than the Raman scattering boosting effects obtained with the conventional technique wherein the surface recesses and protrusions are formed at random.

As described above, with this embodiment of the device for Raman spectroscopy 1, the effects are capable of being obtained in that the intra-plane uniformity of the Raman scattering intensity is capable of being kept high, and the Raman spectrometry is capable of being performed reliably. Further, with this embodiment of the device for Raman spectroscopy 1, by virtue of the high intra-plane uniformity of the recess-protrusion pattern of the light scattering surface 1s, the effects are capable of being obtained in that it is possible to obtain the Raman scattering boosting effects larger than the Raman scattering boosting effects obtained with the conventional technique in which the surface recesses and protrusions are formed at random. Since the aforesaid effects are capable of being obtained together, the high-accuracy Raman spectrometry is capable of being performed reliably such that the data reliability is capable of being kept high and such that the data reproducibility is capable of being kept good.

Further, with this embodiment of the device for Raman spectroscopy 1, by the utilization of the characteristics of the anodic oxidation processing in that the alumina layer having the regular array characteristics is capable of being formed, the alumina layer 30 having been formed with the anodic oxidation processing is removed, and only the un-anodized part of the metal body 10 to be subjected to the anodic oxidation processing is allowed to remain. In this manner, the fine structure body 11 having the dimple-shaped recess areas 12, 12, . . . arrayed regularly is obtained. With the anodic oxidation processing, the metal body 10 to be subjected to the anodic oxidation processing is set as the anode and immersed in the electrolyte, and the voltage is applied across the anode and the cathode. The alumina layer 30 having the regular array characteristics is thus capable of being formed easily. Therefore, the fine structure body 11 having the dimple-shaped recess areas 12, 12, . . . arrayed regularly is capable of being obtained with the simple process and at a low cost. Also, with the adjustment of the conditions for the anodic oxidation processing, the pitches P and the depths of the dimple-shaped recess areas 12, 12, . . . are capable of being controlled easily. Further, the entire area of the surface of the metal body 10 to be subjected to the anodic oxidation processing is capable of being processed in one lot, and therefore the metal body having a large area is capable of being processed appropriately.

In this embodiment of the device for Raman spectroscopy 1, the metal body 10 to be subjected to the anodic oxidation processing contains Al as the principal constituent. Alternatively, the metal body 10 to be subjected to the anodic oxidation processing may contain at least one of various other metals capable of being subjected to the anodic oxidation processing. Examples of the metals other than Al, which are capable of being subjected to the anodic oxidation processing, include Ti, Ta, Hf, and Zr. The metal body 10 to be subjected to the anodic oxidation processing may contain at least two kinds of the metals capable of being subjected to the anodic oxidation processing.

The plane pattern of the formed recess areas varies for different kinds of the metals to be subjected to the anodic oxidation processing. However, in cases where one of the different kinds of the metals to be subjected to the anodic oxidation processing is utilized, the array structure region having the structure, in which the plurality of the dimple-shaped recess areas 12, 12, . . . having the approximately identical shapes, as viewed from above, are arrayed so as to stand close to one another, is capable of being formed as in the embodiment described above.

Second Embodiment of the Device for Raman Spectroscopy

A second embodiment of the device for Raman spectroscopy in accordance with the present invention will be described hereinbelow with reference to FIG. 3A and FIG. 3B. FIG. 3A is a sectional view corresponding to FIG. 2C and showing the un-anodized part of the metal body to be subjected to the anodic oxidation processing and a remainder of the metal oxide layer, which remainder remains after a part of the metal oxide layer has been removed from the metal body to be subjected to the anodic oxidation processing. FIG. 3B is a sectional view corresponding to FIG. 2D and showing the un-anodized part of the metal body to be subjected to the anodic oxidation processing and the remainder of the metal oxide layer, the remainder having a surface, to which a Raman scattering boosting substance has been fixed.

As illustrated in FIG. 3B, as in the first embodiment of the device for Raman spectroscopy in accordance with the present invention, a device for Raman spectroscopy 2, which is a second embodiment of the device for Raman spectroscopy in accordance with the present invention, is provided with a light scattering surface 2s for scattering the incident light.

The device for Raman spectroscopy 2 is primarily constituted of a fine structure body 14. The fine structure body 14 comprises an un-anodized part 11' of the metal body 10 to be subjected to the anodic oxidation processing. The fine structure body 14 also comprises a remainder 30r of the alumina layer 30. The un-anodized part 11' and the remainder 30r remain after the processing has been performed, wherein the anodic oxidation processing is performed on the metal body 10 to be subjected to the anodic oxidation processing as illustrated in FIG. 2A and FIG. 2B, and wherein, instead of the thus formed alumina layer 30 being removed completely, a part of the alumina layer 30, which part extends in the depth direction of the alumina layer 30, is removed as illustrated in FIG. 3A.

As described above with reference to the first embodiment, the alumina layer 30 having been formed with the anodic oxidation processing has the structure, in which the fine pillar-shaped bodies 31, 31, . . . having the approximately regular hexagon shapes, as viewed from above, are arrayed so as to stand close to one another. At the approximately middle area of each of the fine pillar-shaped bodies 31, 31, . . . , the fine hole 32 extending in the depth direction from the surface 10s is formed. Therefore, the remainder 30r of the alumina layer 30 has the constitution corresponding to the constitution of the alumina layer 30. Specifically, the fine structure body 14 is provided with an array structure region 15, in which the fine holes 32, 32, . . . acting as the recess areas and having the approximately identical shapes (i.e, the approximately circular shapes), as viewed from above, are regularly arrayed at the approximately identical pitches. The pitches of the fine holes 32, 32, . . . are identical with the pitches of the fine holes 32, 32, . . . in the first embodiment described above. The fine holes 32, 32, . . . will hereinbelow be referred to as the recess areas 32, 32, . . .

In the second embodiment, as illustrated in FIG. 3B, the Raman scattering boosting substance 20 is fixed to the surface of the array structure region 15 and along the surface recess-protrusion shape of the array structure region 15. In the second embodiment, since the array structure region 15 is constituted of alumina, i.e. the nonmetal, the Raman scattering boosting substance 20 should preferably be Au, Ag, Cu, Pt, Ni, Ti, Al, or the like. The Raman scattering boosting substance 20 should more preferably be Au, Ag, or the like.

This embodiment of the device for Raman spectroscopy 2 primarily comprises the fine structure body 14 provided with the array structure region 15, in which the recess areas 32, 32, . . . are regularly arrayed at the approximately identical pitches. Also, the Raman scattering boosting substance 20 is fixed to the surface of the array structure region 15 and along the surface shape of the array structure region 15. Therefore, the light scattering surface 2s has the surface recess-protrusion shape pattern identical with the surface recess-protrusion shape pattern of the array structure region 15 of the fine structure body 14.

The device for Raman spectroscopy 2 thus has the light scattering surface 2s having the nano-order recess-protrusion pattern. Also, the Raman scattering boosting substance 20 is fixed to the array structure region 15. Therefore, as in the first embodiment described above, the device for Raman spectroscopy 2 has the large Raman scattering boosting effects due to the increase in the surface area by virtue of the surface recess-protrusion pattern and due to the localized plasmon resonance phenomenon. With the aforesaid first embodiment, wherein the array structure region 13 is constituted of the metal (i.e., Al), in cases where the Raman scattering boosting substance 20 is not fixed to the surface of the array structure region 13, the sufficient Raman scattering boosting effects are capable of being obtained. However, in the second embodiment, wherein the array structure region 15 is constituted of the nonmetal, i.e. alumina, it is necessary for the Raman scattering boosting substance 20 to be fixed to the surface of the array structure region 15, such that good Raman scattering boosting effects may be obtained.

With this embodiment of the device for Raman spectroscopy 2, as in the aforesaid first embodiment, the light scattering surface 2s has high intra-plane uniformity of the recess-protrusion pattern. Therefore, the intra-plane uniformity of the Raman scattering intensity is capable of being kept high, and the Raman spectrometry is capable of being performed reliably. Further, with this embodiment of the device for Raman spectroscopy 2, wherein the light scattering surface 2s has high intra-plane uniformity of the recess-protrusion pattern, it is presumed that the localized plasmon resonance phenomenon occurs efficiently. Therefore, as in the aforesaid first embodiment, it is possible to obtain the Raman scattering boosting effects larger than the Raman scattering boosting effects obtained with the conventional technique in which the surface recesses and protrusions are formed at random. Accordingly, as with the first embodiment described above, the high-accuracy Raman spectrometry is capable of being performed reliably such that the data reliability is capable of being kept high and such that the data reproducibility is capable of being kept good.

Further, with this embodiment of the device for Raman spectroscopy 2, by the utilization of the characteristics of the anodic oxidation processing in that the alumina layer having the regular array characteristics is capable of being formed, the part of the alumina layer 30 having been formed with the anodic oxidation processing is removed in the depth direction of the alumina layer 30, and the remaining area is utilized for constituting the fine structure body 14. Therefore, as in the first embodiment described above, the fine structure body 14 having the recess areas 32, 32, . . . arrayed regularly is capable of being obtained with the simple process and at a low cost. Further, the entire area of the surface of the metal body 10 to be subjected to the anodic oxidation processing is capable of being processed in one lot, and therefore the metal body having a large area is capable of being processed appropriately.

In this embodiment of the device for Raman spectroscopy 2, the metal body 10 to be subjected to the anodic oxidation processing contains Al as the principal constituent. Alternatively, as in the first embodiment described above, the metal body 10 to be subjected to the anodic oxidation processing may contain at least one of various other metals capable of being subjected to the anodic oxidation processing. Also, the metal body 10 to be subjected to the anodic oxidation processing may contain at least two kinds of the metals capable of being subjected to the anodic oxidation processing.

In each of the first and second embodiments described above, the dimple-shaped recess areas 12, 12, . . . or the recess areas 32, 32, . . . are arrayed regularly by the utilization of the anodic oxidation processing. The device for Raman spectroscopy in accordance with the present invention has the novel features in that the device for Raman spectroscopy comprises the fine structure body provided with the array structure region, in which the plurality of the recess areas having the approximately identical shapes, as viewed from above, are arrayed regularly at the approximately identical pitches, and in that the surface of the fine structure body on the side of the array structure region acts as the light scattering surface. It is sufficient for the array structure region of the fine structure body to be formed over at least the range, to which the light is irradiated at the time of the Raman spectrometry.

In order for the fine structure body provided with the array structure region, in which the plurality of the recess areas are arrayed regularly, to be obtained, besides the technique for utilizing the anodic oxidation processing, one of various other fine processing technologies may be employed. For example, a fine processing technology may be employed, wherein a plurality of recess areas arrayed regularly are formed with a nano-imprinting process on the surface of a base body made from a resin, or the like. Alternatively, a fine processing technology maybe employed, wherein a plurality of recess areas arrayed regularly are drawn on the surface of a base body made from a metal, or the like, by the utilization of an electron drawing process using a focused ion beam (FIB) or an electron beam (EB).

With one of various fine processing technologies, the device for Raman spectroscopy in accordance with the present invention is formed so as to have the constitution, in which the recess areas are arrayed regularly, and in which the regular surface recess-protrusion structure is formed. Therefore, the device for Raman spectroscopy in accordance with the present invention has the advantages over the conventional technique described in, for example, Japanese Unexamined Patent Publication No. 2004-170334, wherein the metal-coated fine particles are fixed to the surface of the base plate, and wherein the regular surface recess-protrusion structure is thereby formed, in that the device for Raman spectroscopy is capable of being produced easily. Particularly, the first and second embodiments described above, in which the anodic oxidation processing is utilized, have the advantages in that the entire area of the surface of the metal body to be subjected to the anodic oxidation processing is capable of being processed in one lot, in that the metal body having a large area is capable of being processed appropriately, and in that the device for Raman spectroscopy is capable of being produced by use of a low-cost production apparatus.

In each of the first and second embodiments described above, the Raman scattering boosting substance 20 is fixed to the entire area of the surface of the array structure region 13 of the fine structure body 11 or to the entire area of the surface of the array structure region 15 of the fine structure body 14. Alternatively, by the adjustment of the application, or the like, of the Raman scattering boosting substance 20, the fixing of the Raman scattering boosting substance 20 may be performed such that the Raman scattering boosting substance 20 is isolated at each of the dimple-shaped recess areas 12, 12, . . . or at each of the recess areas 32, 32, . . . In such cases, the localized plasmon resonance occurs more strongly, and the Raman scattering boosting effects are capable of being enhanced even further. In cases where the constitution, in which the Raman scattering boosting substance 20 is isolated at each of the dimple-shaped recess areas 12, 12, . . . or at each of the recess areas 32, 32, . . . , is employed, it is expected that the Raman scattering boosting effects $10^{11}$ to $10^{14}$ times as large as the Raman scattering measured from only the substance (the sample) are capable of being obtained. (As for the expectation described above, reference may be made to, for example, "Modern Chemistry," p. 20, Sep. 2003.)

Embodiment of Raman Spectroscopic Apparatus

An embodiment of the Raman spectroscopic apparatus in accordance with the present invention, in which the aforesaid first embodiment of the device for Raman spectroscopy 1 is employed, will be described hereinbelow with reference to FIG. 4. FIG. 4 is a sectional view corresponding to FIG. 1B showing the first embodiment of the device for Raman spectroscopy 1. In cases where the aforesaid second embodiment of the device for Raman spectroscopy 2 is employed, the Raman spectroscopic apparatus may be constituted basically in the same manner as that for the Raman spectroscopic apparatus in accordance with the present invention, in which the aforesaid first embodiment of the device for Raman spectroscopy 1 is employed.

With reference to FIG. 4, a Raman spectroscopic apparatus 3 comprises a vessel 40, in which the device for Raman spectroscopy 1 is located. The Raman spectroscopic apparatus 3 also comprises light irradiating means 50 for irradiating light, which has a specific wavelength, to the light scattering surface 1s of the device for Raman spectroscopy 1. The Raman spectroscopic apparatus 3 further comprises spectroscopic means 60 for separating the scattered light, which occurs at the light scattering surface 1s, into spectral components of the scattered light, and obtaining a spectrum of Raman scattered light.

The vessel 40 has a box-like shape. The device for Raman spectroscopy 1 having the light scattering surface 1s, on which a sample (not shown) has been located, is located on a bottom surface of the vessel 40. A transparent window 41 is fitted into a top surface of the vessel 40 and at the position which stands facing the light scattering surface 1s of the device for Raman spectroscopy 1.

The light irradiating means 50 comprises a light source (not shown), such as a laser. The light irradiating means 50 also comprises light guide system (not shown) for guiding the light having been produced by the light source. The light irradiating means 50 is located on the side outward from the vessel 40 and irradiates the light having the specific wavelength to the light scattering surface 1s of the device for Raman spectroscopy 1 via the transparent window 41 of the vessel 40.

The spectroscopic means 60 comprises a spectrophotometer (not shown), and the like. The spectroscopic means 60 separates the scattered light, which occurs at the light scattering surface 1s of the device for Raman spectroscopy 1, into the spectral components of the scattered light and obtains the spectrum (i.e., the Raman spectrum) of the Raman scattered light. The spectroscopic means 60 is located on the side outward from the vessel 40, such that the scattered light, which occurs at the light scattering surface 1s of the device for Raman spectroscopy 1, impinges upon the spectroscopic means 60 via the transparent window 41 of the vessel 40.

With this embodiment of the Raman spectroscopic apparatus 3 having the constitution described above, the light having the specific wavelength, which light has been irradiated from the light irradiating means 50 to the light scattering surface 1s of the device for Raman spectroscopy 1, is scattered from the light scattering surface 1s, which stands facing the sample. The scattered light having thus occurred impinges upon the spectroscopic means 60. The scattered light is separated by the spectroscopic means 60 into the spectral components of the scattered light, and the Raman spectrum is formed by the spectroscopic means 60. The Raman spectrum varies for different kinds of samples to be measured. Therefore, by the formation of the Raman spectrum, the identification of the substance, or the like, is capable of being performed.

For example, the measurement may be made in a state in which a known antibody has been fixed to the light scattering surface 1s of the device for Raman spectroscopy 1. In such cases, if an antigen is contained in the sample, binding of the antibody and the antigen with each other will occur, and the obtained Raman spectrum will alter. Therefore, in accordance with the alteration of the Raman spectrum, the identification of the antigen is capable of being performed. In cases where the measurement is made in a state in which a known antigen has been fixed to the light scattering surface 1s of the device for Raman spectroscopy 1, the identification of the antibody is capable of being performed in accordance with the alteration of the Raman spectrum.

This embodiment of the Raman spectroscopic apparatus 3 is constituted by the utilization of the device for Raman spectroscopy 1. Therefore, with the Raman spectroscopic apparatus 3, the high-accuracy Raman spectrometry is capable of being performed reliably such that the data reliability is capable of being kept high and such that the data reproducibility is capable of being kept good. With the Raman spectroscopic apparatus 3, where in the device for Raman spectroscopy 1 having the high intra-plane uniformity of the recess-protrusion pattern is employed, in cases where measurements are performed on an identical sample through alteration of the light irradiating site, the data having good reproducibility are capable of being obtained. Therefore, in cases where a plurality of data are obtained with respect to the identical sample and through the alteration of the light irradiating site, the reliability of the data is capable of being enhanced.

The present invention will further be illustrated by the following non-limitative examples.

EXAMPLES

Examples 1 and 2

In each of Examples 1 and 2, a device for Raman spectroscopy 1, which was the first embodiment of the device for Raman spectroscopy in accordance with the present invention, was produced in the manner described below.

An aluminum plate (Al purity: 99.99%, thickness: 10 mm) was prepared as the metal body 10 to be subjected to the anodic oxidation processing. The aluminum plate was set as an anode, and aluminum was set as a cathode. The anodic oxidation processing was thus performed under conditions such that a part of the aluminum plate was converted into the alumina layer 30. The liquid temperature was set at 15° C. The other reaction conditions were set as shown below.

Example 1

Electrolyte: 0.3 M sulfuric acid
Applied voltage: 25V
Reaction time: eight hours Example 2

Electrolyte: 0.5 M oxalic acid
Applied voltage: 40V
Reaction time: five hours

In each of Examples 1 and 2, after the reaction was finished, wet etching processing was performed by use of a chromic acid solution, and the alumina layer 30 was thereby removed. In this manner, the fine structure body 11 constituted of an un-anodized part was obtained.

An SEM observation of the surface of the fine structure body 11, which was thus obtained in each of Examples 1 and 2, revealed that the surface of the fine structure body 11 had a surface structure, in which the dimple-shaped recess areas 12, 12, . . . having approximately regular hexagon shapes, as viewed from above, were arrayed regularly. In each of Examples 1 and 2, the pitches P of the dimple-shaped recess areas 12, 12, . . . were as shown below.

Example 1

Pitches P: 63 nm

Example 2

Pitches P: 100 nm

Though not measured, it was presumed that the depths of the dimple-shaped recess areas 12, 12, . . . in Example 1 fell within the range of approximately 5 nm to approximately 15 nm. Also, it was presumed that the depths of the dimple-shaped recess areas 12, 12, . . . in Example 2 fell within the range of approximately 5 nm to approximately 20 nm.

In each of Examples 1 and 2, gold acting as the Raman scattering boosting substance 20 was overlaid on the surface of the obtained fine structure body 11 with vacuum evaporation processing, and the device for Raman spectroscopy 1 in accordance with the present invention was thereby obtained. The vacuum evaporation processing was performed under the conditions such that the gold thickness at the middle part of each of the dimple-shaped recess areas 12, 12, . . . became equal to 10 nm, and such that the entire area of the surface of the fine structure body 11 was covered with gold (as illustrated in FIG. 1B).

Comparative Examples 1 and 2

In each of Comparative Examples 1 and 2, gold was overlaid on a glass base plate with the vacuum evaporation processing, and an island-shaped vacuum deposited film, which had been reported as having the surface boosted Raman effects, was thereby formed. The vacuum evaporation processing with gold was performed under the conditions identical with the conditions of the vacuum evaporation processing with gold performed in each of Examples 1 and 2, and the vacuum deposited film having a thickness of 10 nm was thereby formed. Thereafter, in each of Comparative Examples 1 and 2, annealing was performed under the conditions shown below, and a device for Raman spectroscopy for comparison was thus obtained.

Comparative Example 1

Annealing at a temperature of 500° C. for five minutes was performed one time.

Comparative Example 2

Annealing at a temperature of 500° C. for five minutes was performed two times. (The second annealing was performed after the first annealing had been finished and after the temperature had been lowered to normal temperatures.)

(Evaluation)

An identical liquid sample was applied onto the device for Raman spectroscopy having been obtained in each of Examples 1 and 2 and each of Comparative Examples 1 and 2, and a measurement of the Raman spectrum was made by use of a Raman spectroscopic apparatus (HR800, supplied by Horiba, Ltd.), which had an apparatus constitution identical with the apparatus constitution of the Raman spectroscopic apparatus 3 shown in FIG. 4. In the measurement with respect to the device for Raman spectroscopy having been obtained in each of Examples 1 and 2 and each of Comparative Examples 1 and 2, a laser for producing a laser beam having a wavelength of 532 nm was employed as the light source, and the intensity of the produced laser beam was set at an identical intensity. As the spectroscopic means 60 illustrated in FIG. 4, a spectrophotometer of a 150 L/mm type was utilized. As the liquid sample, an R6G solution having been diluted to several mM was utilized. It had been known that R6G had the characteristics such that a Raman spectrum peak appeared at approximately 1,360 $cm^{-1}$.

FIG. 5 is a diagram showing Raman spectra obtained with devices for Raman spectroscopy produced in Examples 1 and 2 and Comparative Examples 1 and 2. (The measurement wavelength was 785 nm.) In FIG. 5, the intensity plotted on the vertical axis is graduated in 500 (a. u.). As clear from FIG. 5, with each of the devices for Raman spectroscopy produced in Examples 1 and 2, the signal at 1,360 cm$^{-1}$ was boosted more strongly than with each of the devices for Raman spectroscopy produced in Comparative Examples 1 and 2. The effects of the device for Raman spectroscopy in accordance with the present invention were thus capable of being confirmed.

INDUSTRIAL APPLICABILITY

The device for Raman spectroscopy in accordance with the present invention is applicable to Raman spectroscopic apparatuses, wherein scattered light, which is obtained from irradiation of single-wavelength light to a substance, is separated into spectral components of the scattered light, wherein a Raman spectrum of Raman scattered light is thereby obtained, and wherein identification of a substance, or the like, is performed in accordance with the obtained Raman spectrum.

What is claimed is:

1. A device for Raman spectroscopy, which is adapted for use in Raman spectroscopy for separating scattered light into its spectral components and detecting Raman scattered light, and which is provided with a light scattering surface for scattering incident light, wherein:
   the device for Raman spectroscopy comprises a fine structure body provided with an array structure region, in which a plurality of recess areas having approximately identical shapes, as viewed from above, are arrayed regularly at approximately identical pitches,
   a surface of the fine structure body on the side of the array structure region acts as the light scattering surface, and
   the entire light scattering surface is a metal surface.

2. A device for Raman spectroscopy as defined in claim 1 wherein a Raman scattering boosting substance, which exhibits a Raman scattering intensity higher than the Raman scattering intensity of a constituent material of the array structure region, is fixed to the array structure region side of the fine structure body.

3. A device for Raman spectroscopy as defined in claim 1, wherein the fine structure body is formed from a metal body that contains aluminum as a principal constituent, and the recess areas have approximately regular hexagon shapes, as viewed from above, and are arrayed so as to stand close to one another.

4. A device for Raman spectroscopy as defined in claim 3, wherein the fine structure body is formed by:
   performing anodic oxidation processing on the metal body, wherein a part of the metal body is converted into a metal oxide layer, and
   removing the metal oxide layer from the metal body.

5. A device for Raman spectroscopy as defined in claim 3, wherein the fine structure body is formed by:
   performing anodic oxidation processing on the metal body, wherein a part of the metal body is converted into a metal oxide layer,
   removing a part of the metal oxide layer, and
   coating an uneven surface formed on the remaining part of the metal oxide layer with a metal.

6. A Raman spectroscopic apparatus, comprising:
   i) a device for Raman spectroscopy as defined in claim 1,
   ii) light irradiating means for irradiating light, which has a specific wavelength, to the light scattering surface of the device for Raman spectroscopy, and
   iii) spectroscopic means for separating the scattered light, which occurs at the light scattering surface, into spectral components of the scattered light, and obtaining a spectrum of Raman scattered light.

7. A method for producing a device for Raman spectroscopy, which is adapted for use in Raman spectroscopy for separating scattered light into its spectral components and detecting Raman scattered light, and which is provided with a light scattering surface for scattering incident light, the method comprising:
   performing anodic oxidation processing on a metal body, comprising converting a part of the metal body into a metal oxide layer;
   removing a part of the metal oxide layer from the metal body; and
   coating an uneven surface formed on the remaining part of the metal oxide layer with a metal.

8. A device for Raman spectroscopy as defined in claim 1, wherein the metal surface is formed on a dielectric material.

* * * * *